(12) United States Patent
Luo et al.

(10) Patent No.: US 11,529,321 B2
(45) Date of Patent: *Dec. 20, 2022

(54) USE OF AMINOMETHYLENECYCLOHEXANE-1,3-DIONE COMPOUND

(71) Applicant: WIGEN BIOMEDICINE TECHNOLOGY (SHANGHAI) CO., LTD., Shanghai (CN)

(72) Inventors: Cheng Luo, Shanghai (CN); Liyan Yue, Shanghai (CN); Wei Wan, Shanghai (CN); Yuanyuan Zhang, Shanghai (CN); Hualiang Jiang, Shanghai (CN); Kaixian Chen, Shanghai (CN)

(73) Assignee: WIGEN BIOMEDICINE TECHNOLOGY (SHANGHAI) CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/614,521

(22) PCT Filed: May 18, 2018

(86) PCT No.: PCT/CN2018/087452
§ 371 (c)(1),
(2) Date: Nov. 18, 2019

(87) PCT Pub. No.: WO2018/214814
PCT Pub. Date: Nov. 29, 2018

(65) Prior Publication Data
US 2020/0170966 A1    Jun. 4, 2020

(30) Foreign Application Priority Data

May 22, 2017  (CN) .......................... 201710364909.9

(51) Int. Cl.
| | | |
|---|---|---|
| *A61K 31/135* | (2006.01) | |
| *A61K 31/133* | (2006.01) | |
| *A61K 31/17* | (2006.01) | |
| *A61K 31/18* | (2006.01) | |
| *A61K 31/341* | (2006.01) | |
| *A61K 31/415* | (2006.01) | |
| *A61K 31/4166* | (2006.01) | |
| *A61K 31/4525* | (2006.01) | |
| *A61K 31/497* | (2006.01) | |
| *A61K 31/5375* | (2006.01) | |
| *A61K 45/06* | (2006.01) | |

(52) U.S. Cl.
CPC .......... *A61K 31/135* (2013.01); *A61K 31/133* (2013.01); *A61K 31/17* (2013.01); *A61K 31/18* (2013.01); *A61K 31/341* (2013.01); *A61K 31/415* (2013.01); *A61K 31/4166* (2013.01); *A61K 31/4525* (2013.01); *A61K 31/497* (2013.01); *A61K 31/5375* (2013.01); *A61K 45/06* (2013.01)

(58) Field of Classification Search
CPC combination set(s) only.
See application file for complete search history.

(56) References Cited

U.S. PATENT DOCUMENTS

2009/0163545 A1* 6/2009 Goldfarb ................ A61K 31/47
514/312
2015/0166492 A1    6/2015 Cuervo et al.

FOREIGN PATENT DOCUMENTS

| CN | 103977002 A | 8/2014 |
|---|---|---|
| WO | 2011033389 A2 | 3/2011 |

OTHER PUBLICATIONS

Tumor definition in National Cancer Institute—www.cancer.gov—May 22, 2014.*
Stomach cancer—Mayoclinic.com—Apr. 9, 2011.*
GastricMALTLymphoma—LymphomaAssociation—2011.*
"Adult Brain Tumors Treatment", National Cancer Institute, pp. 1-21 (Jan. 24, 2013).*
"Types of Brain Cancer" at http://www.cancercenter.com/brain-cancer/types-of-brain-cancer.cfm (Mar. 12, 2013).*
"Colorectal Cancer" at cancer.net (published Sep. 2012), pp. 1-2.*
"Types of Breast Cancer", published in breastcancer.org (Sep. 30, 2012); p. 1.*
Goldfarb "809" and "775" assays for compound 128—Date 2007.*

(Continued)

*Primary Examiner* — Valerie Rodriguez-Garcia
(74) *Attorney, Agent, or Firm* — SZDC Law P.C.

(57) ABSTRACT

The present invention relates to use of an aminomethylene-cyclohexane-1,3-dione compound, more particularly to use of a compound shown in the following formula (I) or a pharmaceutically acceptable salt thereof alone or in combination with other drug in preparing a drug for regulating or treating a disease related to autophagy, especially mammalian ATG8 homologous proteins.

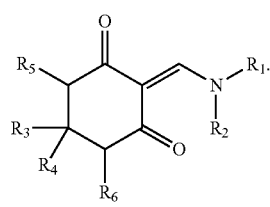

(I)

2 Claims, 2 Drawing Sheets
Specification includes a Sequence Listing.

(56) References Cited

OTHER PUBLICATIONS

PubChem AID 809—for compound of SID No. 7975442. Goldfarb "809" assay compound 245—Date 2007.*

Canela, M.D. et al., "Targeting the Colchicine Site in Tubulin through Cyclohexanedione Dervatives" RSC Advances, vol. 6, No. 23, Feb. 9, 2016.

Maria-Dolores Canela et al. "Novel Colchicine-Site Binders with a Cyclohexanedione Scaffold Identified through a Ligand-Based Virtual Screening Approach" J. Med. Chem. 2014, 57, 3924-3938 (Apr. 28, 2014).

* cited by examiner

SEQUENCE LISTING

<160> NUMBER OF SEQ ID NOS: 2

<210> SEQ ID NO 1
<211> LENGTH: 356
<212> TYPE: PRT
<213> ORGANISM: Artificial Sequence
<220> FEATURE:
<223> OTHER INFORMATION: GST-LC3B

<400> SEQUENCE: 1

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu

```
210                 215                 220
Phe Gln Gly Pro Leu Gly Ser Met Pro Ser Glu Lys Thr Phe Lys Gln
225                 230                 235                 240

Arg Arg Thr Phe Glu Gln Arg Val Glu Asp Val Arg Leu Ile Arg Glu
                245                 250                 255

Gln His Pro Thr Lys Ile Pro Val Ile Ile Glu Arg Tyr Lys Gly Glu
                260                 265                 270

Lys Gln Leu Pro Val Leu Asp Lys Thr Lys Phe Leu Val Pro Asp His
                275                 280                 285

Val Asn Met Ser Glu Leu Ile Lys Ile Ile Arg Arg Arg Leu Gln Leu
                290                 295                 300

Asn Ala Asn Gln Ala Phe Phe Leu Leu Val Asn Gly His Ser Met Val
305                 310                 315                 320

Ser Val Ser Thr Pro Ile Ser Glu Val Tyr Glu Ser Glu Lys Asp Glu
                325                 330                 335

Asp Gly Phe Leu Tyr Met Val Tyr Ala Ser Gln Glu Thr Phe Gly Met
                340                 345                 350

Lys Leu Ser Val
            355

<210> SEQ ID NO 2
<211> LENGTH: 15
<212> TYPE: PRT
<213> ORGANISM: Artificial Sequence
<220> FEATURE:
<223> OTHER INFORMATION: N-terminal FITC-labeled peptide

<400> SEQUENCE: 2

Gly Gly Asp Asp Asp Trp Thr His Leu Ser Ser Lys Glu Val Asp
1               5                   10                  15
```

USE OF AMINOMETHYLENECYCLOHEXANE-1,3-DIONE COMPOUND

This application is the National Stage Application of PCT/CN2018/087452, filed on May 18, 2018, which claims priority to Chinese Patent Application No.: 201710364909.9, filed on May 22, 2017, which is incorporated by reference for all purposes as if fully set forth herein.

FIELD OF THE INVENTION

The present invention relates to the field of biomedicine, and more particularly to use of an aminomethylenecyclohexane-1,3-dione compound or a salt thereof in the preparation of drugs for treating diseases associated with autophagy, particularly a mammalian ATG8 homologous protein.

DESCRIPTION OF THE RELATED ART

Autophagy is a cellular degradative pathway whereby dysfunctional proteins or organelles are transported to lysosome and then digested and degraded. It is a universal and conservative process amongst yeast, plants and mammals.

Current studies demonstrate that autophagy not only plays an important part in maintaining physiological functions, such as providing nutrients during hunger, eliminating cell contents and antigen presentation, but also has key functions in tumors, cardiovascular disease, autoimmune disease, neurodegenerative disease, hypertension, bone tissue cell and bone diseases, Crohn's disease, acute kidney injury, cerebral ischemia, retinal disease, bronchial asthma, Vici syndrome, and various infectious diseases.

In the developing process of tumors, the autophagy functions as a double edged-sword role: in the early stage of tumor development, the autophagy defects may increase genomic instabilities and promote carcinogenesis; in the stage of rapid growth and metastasis of tumors, autophagy can resist stress conditions to inhibit anoikis and maintain tumor cell survival. Although the relationship between autophagy and tumors varies at different stages of tumor development, the development of autophagy regulators will be of great value for advanced cancers and chemotherapy-resistant cancers.

Currently, there are about 30 clinical trials about autophagy regulation, for example, using hydroxychloroquine alone, chloroquine alone or combined with other anti-tumor drugs to assess the therapeutic effects of autophagy inhibition mainly on refractory or relapsed solid tumors. Relevant results can be retrieved on the clinicaltrial.gov website. However, the side effects of antilysosomal agents and undetermined directions of chemical space optimization may severely limit further development of these types of autophagy inhibitors, because of a lack of definite molecular targets.

Small molecule modulators targeting autophagy are focused in mTOR or lysosome modulators at present. Small molecule modulators of autophagy related proteins, like the enzymes ATG4 and ULK1, are still at an early development stage. The modulators for the most important autophagy related proteins, ATG8 and its mammalian homologous family proteins LC3, GABARAP and GATE-16 subfamilies, still have not been reported. In human body, the LC3 family includes LC3A, LC3B and LC3C; the GABARAP family includes GABARAPL and GABARAPL1; and the GATE-16 family includes GABARAPL2. LC3B is undoubtedly the one has been studied most completely among the ATG8 mammalian homologous proteins, and it is believed to be a marker of autophagy. There are no reports on modulators of LC3B at present; therefore, there is an urgent need to develop LC3B modulators for treating autophagy related deceases.

Meanwhile, the composition of compounds modulating autophagy with commercially available drugs has broad application prospect in various tumors, cardiovascular disease, autoimmune disease, neurodegenerative disease, hypertension, bone tissue cell and bone diseases, Crohn's disease, acute kidney injury, cerebral ischemia, retinal disease, bronchial asthma, Vici syndrome, and various infectious diseases.

SUMMARY OF THE INVENTION

In a first aspect, the present invention provides use of a compound of Formula (I) below or a pharmaceutically acceptable salt thereof, alone or in combination with other drugs, in the preparation of drugs for modulating autophagy and treating diseases associated with autophagy:

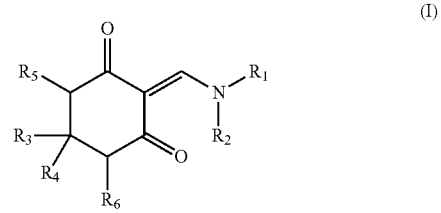

where:

$R_1$ and $R_2$ are each independently selected from the group consisting of hydrogen, hydroxyl, amino, cyano, formyl, $C_{1-6}$ alkyl, $C_{1-6}$ haloalkyl, $C_{1-6}$ alkoxy, $C(=O)R_a$, $SO_2R_a$, substituted or unsubstituted $-(CH_2)_m-C_{5-10}$ aryl or 5-10 membered heteroaryl, and substituted or unsubstituted $-(CH_2)_m-C_{3-7}$ cycloalkyl and 3-7 membered heterocyclyl, in which $R_a$ is selected from the group consist of hydrogen, hydroxyl, $C_{1-6}$ alkyl, $C_{1-6}$ haloalkyl, substituted or unsubstituted $C_{1-6}$ hydroxyalkyl, substituted or unsubstituted amino, substituted or unsubstituted phenyl, and substituted or unsubstituted 5- to 6-membered heteroaryl; and $R_3$, $R_4$, $R_5$, and $R_6$ are each independently selected from the group consist of hydrogen, hydroxyl, amino, halo, cyano, nitro, carboxyl, formyl, amido, an ester group, $C_{1-6}$ alkyl, $C_{1-6}$ haloalkyl, $C_{1-6}$ alkoxy, substituted or unsubstituted $C_{6-10}$ aryl, substituted or unsubstituted 5-10 membered heteroaryl, $C_{3-7}$ cycloalkyl, and 3-7 membered heterocyclyl;

where the halo is selected from F, Cl, Br, or I, and preferably F, Cl, or Br;

the term "substituted" indicates that the group is substituted with one or more substituents selected from the group consist of hydroxyl, amino ($-NH_2$), cyano, halo, nitro, trifluoromethyl, carboxyl, an ester group, formyl, $C_{1-6}$ alkyl, $C_{1-6}$ haloalkyl, $C_{1-6}$ hydroxyalkyl, $C_{1-6}$ alkoxy, 3-10 membered heterocyclyl, $C_{6-10}$ aryl, and 5-10 membered heteroaryl; and m is selected from 0, 1, 2, and 3, and preferably 1 or 2.

In a preferred embodiment, the $C_{5-10}$ aryl or 5-10 membered heteroaryl is preferably selected from a group formed by removing one hydrogen atom from the following rings:

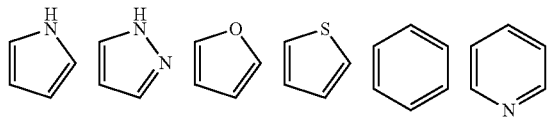

-continued and
the C$_{3-7}$ cycloalkyl or 3-7 membered heterocyclyl is preferably selected from a group formed by removing one hydrogen atom from the following rings:

In a preferred embodiment, the compound of General Formula (I) is selected from the following compounds:

| Compound | Structure |
|---|---|
| 1 | 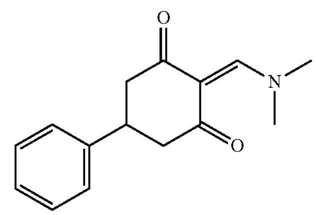 [SMILES: CN(C)C=C1C(=O)CC(c2ccccc2)CC1=O] |
| 2 | 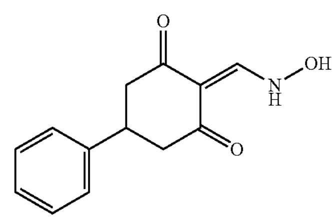 [SMILES: O=C1CC(c2ccccc2)CC(=O)C1=CNO] |
| 3 | 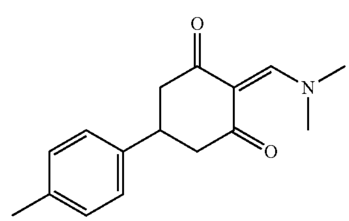 |
| 4 | 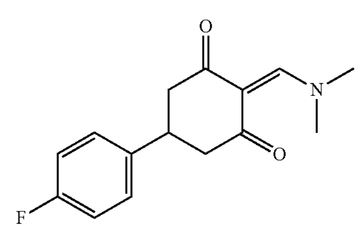 [SMILES: CN(C)C=C1C(=O)CC(c2ccc(F)cc2)CC1=O] |
| 5 | 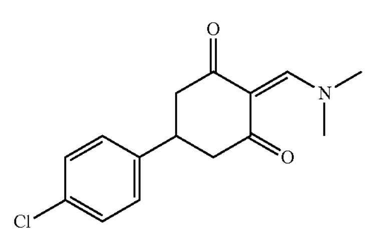 [SMILES: CN(C)C=C1C(=O)CC(c2ccc(Cl)cc2)CC1=O] |

-continued

| Compound | Structure |
|---|---|
| 6 | 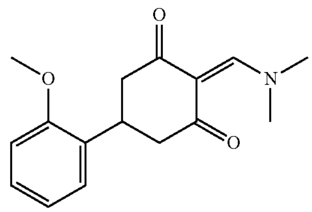 [SMILES: COc1ccccc1C1CC(=O)C(=CN(C)C)C(=O)C1] |
| 7 | 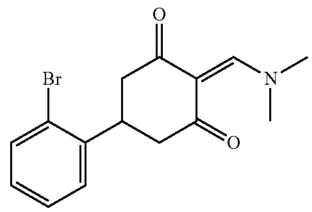 [SMILES: CN(C)C=C1C(=O)CC(c2ccccc2Br)CC1=O] |
| 8 | 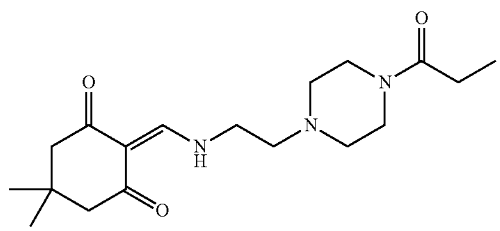 [SMILES: CCC(=O)N1CCN(CCNC=C2C(=O)CC(C)(C)CC2=O)CC1] |
| 9 | 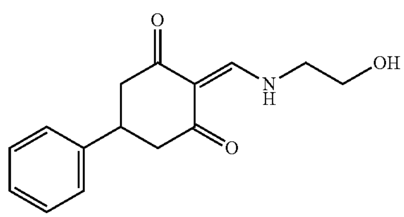 [SMILES: O=C1CC(c2ccccc2)CC(=O)C1=CNCCO] |
| 10 | 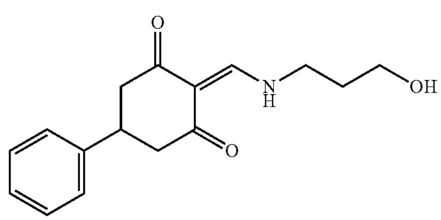 [SMILES: O=C1CC(c2ccccc2)CC(=O)C1=CNCCCO] |
| 11 | 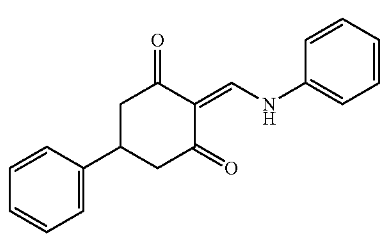 [SMILES: O=C1CC(c2ccccc2)CC(=O)C1=CNc1ccccc1] |
| 12 | 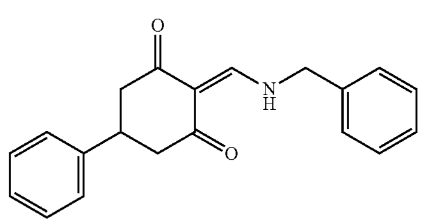 [SMILES: O=C1CC(c2ccccc2)CC(=O)C1=CNCc1ccccc1] |

| Compound | Structure |
|---|---|
| 13 | 2-{[(pyridin-2-ylmethyl)amino]methylidene}-5-phenylcyclohexane-1,3-dione |
| 14 | 2-{[(1,2,3,4-tetrahydroisoquinolin-1-ylmethyl)amino]methylidene}-5-(thiophen-2-yl)cyclohexane-1,3-dione |
| 15 | 2-[(phenylamino)methylidene]-5-(furan-2-yl)cyclohexane-1,3-dione |
| 16 | 2-{[(carboxymethyl)amino]methylidene}-5-phenylcyclohexane-1,3-dione |
| 17 | 2-{[(3-methyl-4-phenyl-1H-pyrazol-5-yl)amino]methylidene}-5,5-dimethylcyclohexane-1,3-dione |
| 18 | 2-[(dimethylamino)methylidene]-5-ethylcyclohexane-1,3-dione |
| 19 | 2-[(dimethylamino)methylidene]-5-propylcyclohexane-1,3-dione |

-continued

| Compound | Structure |
|---|---|
| 20 | *(2-((dimethylamino)methylene)-5-(methoxymethyl)cyclohexane-1,3-dione)* |
| 21 | *(2-((dimethylamino)methylene)-5,5-dimethylcyclohexane-1,3-dione)* |
| 22 | *(5-((dimethylamino)methylene)spiro[2.5]octane-4,6-dione)* |
| 23 | *(2-((dimethylamino)methylene)-4-methylcyclohexane-1,3-dione)* |
| 24 | *(2-((butylamino)methylene)cyclohexane-1,3-dione)* |
| 25 | *(1-(((2,6-dioxocyclohexylidene)methyl)-3-methylurea)* |
| 26 | *(N'-((2,6-dioxocyclohexylidene)methyl)-4-methylbenzenesulfonohydrazide)* |
| 27 | *(5,5-dimethyl-2-(((4-nitrophenyl)amino)methylene)cyclohexane-1,3-dione)* |

-continued
| Compound | Structure |
|---|---|
| 28 | 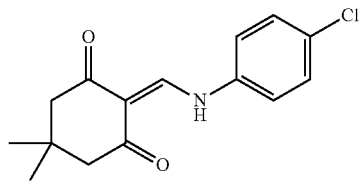 [SMILES: CC1(C)CC(=O)C(=CNc2ccc(Cl)cc2)C(=O)C1] |
| 29 | 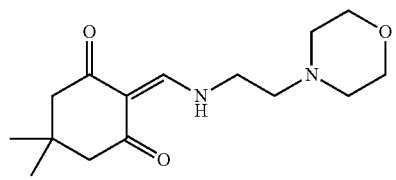 [SMILES: CC1(C)CC(=O)C(=CNCCN2CCOCC2)C(=O)C1] |
| 30 | 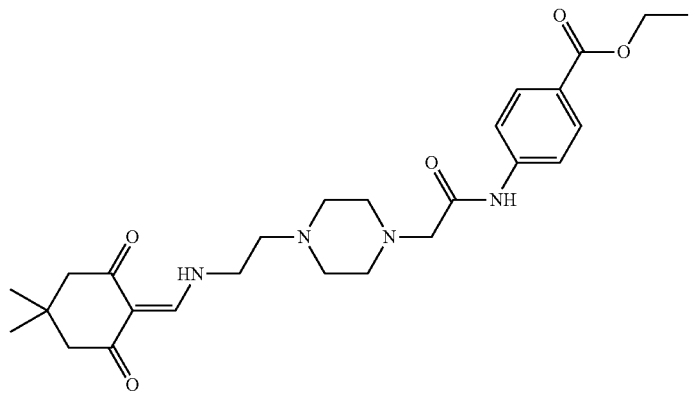 [SMILES: CCOC(=O)c1ccc(NC(=O)CN2CCN(CCNC=C3C(=O)CC(C)(C)CC3=O)CC2)cc1] |
| 31 | 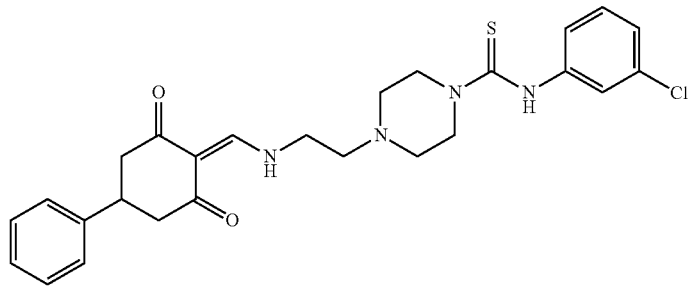 [SMILES: O=C1CC(c2ccccc2)CC(=O)C1=CNCCN1CCN(C(=S)Nc2cccc(Cl)c2)CC1] |
| 32 | 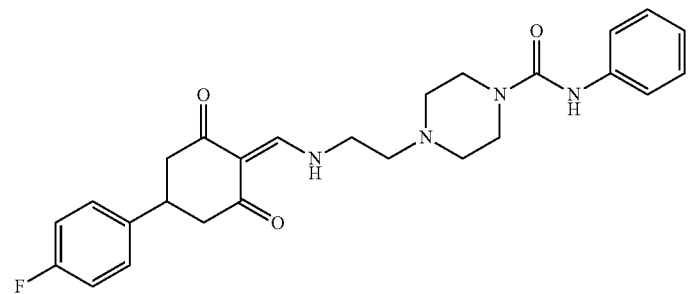 [SMILES: O=C1CC(c2ccc(F)cc2)CC(=O)C1=CNCCN1CCN(C(=O)Nc2ccccc2)CC1] |

-continued

| Compound | Structure |
|---|---|
| 33 | 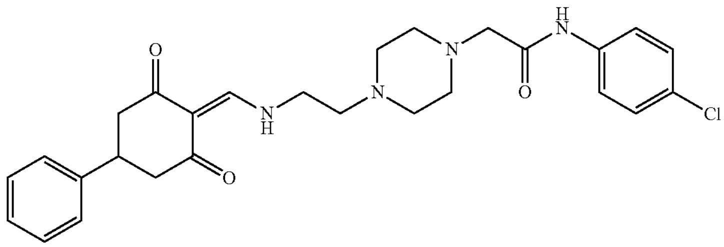 [SMILES: O=C(CN1CCN(CCNC=C2C(=O)CC(c3ccccc3)CC2=O)CC1)Nc1ccc(Cl)cc1] |
| 34 | 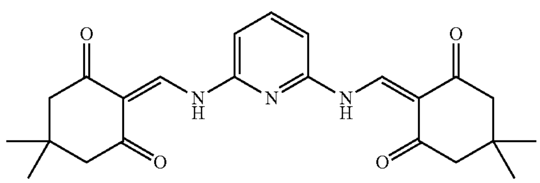 |
| 35 | 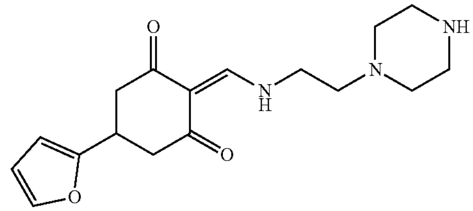 [SMILES: O=C1CC(c2ccco2)CC(=O)C1=CNCCN1CCNCC1] |
| 36 | 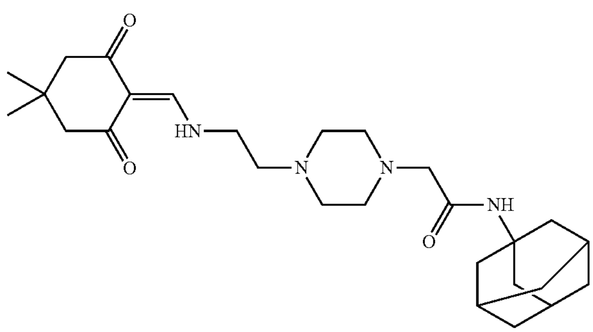 [SMILES: CC1(C)CC(=O)C(=CNCCN2CCN(CC(=O)NC34CC5CC(CC(C5)C3)C4)CC2)C(=O)C1] |
| 37 | 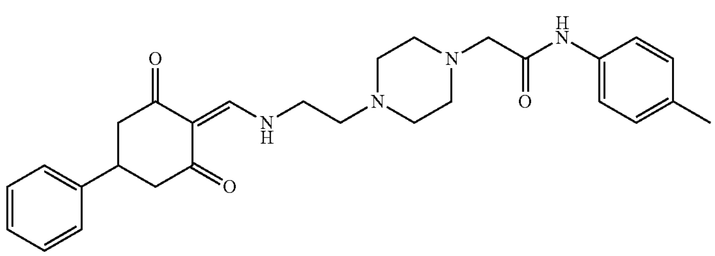 [SMILES: Cc1ccc(NC(=O)CN2CCN(CCNC=C3C(=O)CC(c4ccccc4)CC3=O)CC2)cc1] |
| 38 | 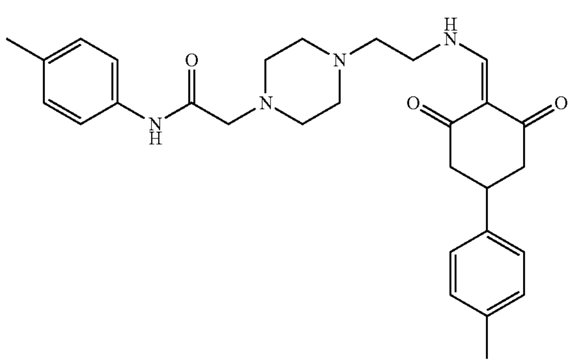 [SMILES: Cc1ccc(NC(=O)CN2CCN(CCNC=C3C(=O)CC(c4ccc(C)cc4)CC3=O)CC2)cc1] |

-continued
| Compound | Structure |
|---|---|
| 39 | 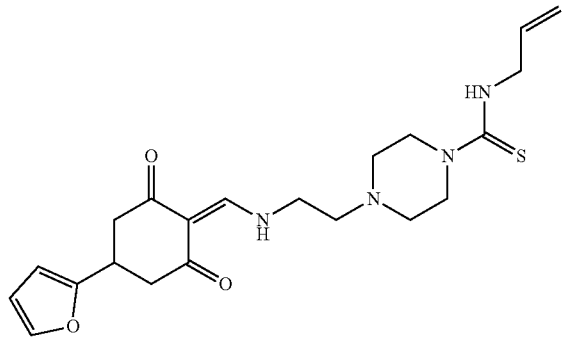 [SMILES: C=CCNC(=S)N1CCN(CCNC=C2C(=O)CC(c3ccco3)CC2=O)CC1] |
| 40 | 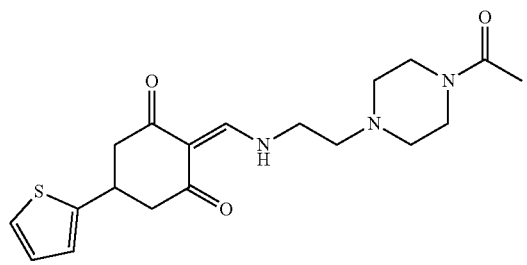 [SMILES: CC(=O)N1CCN(CCNC=C2C(=O)CC(c3cccs3)CC2=O)CC1] |
| 41 | 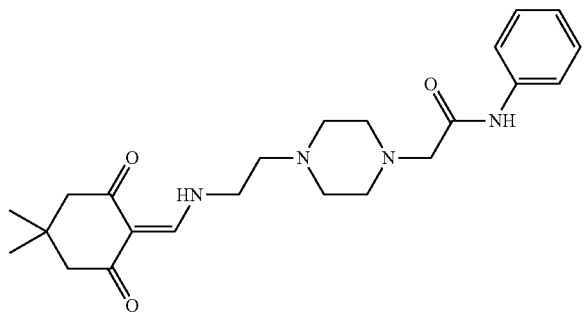 [SMILES: CC1(C)CC(=O)C(=CNCCN2CCN(CC(=O)Nc3ccccc3)CC2)C(=O)C1] |
| 42 | 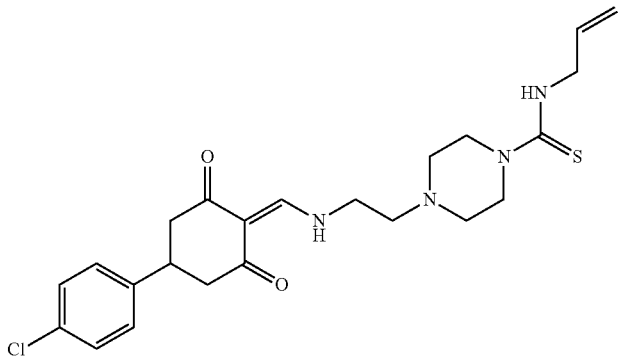 [SMILES: C=CCNC(=S)N1CCN(CCNC=C2C(=O)CC(c3ccc(Cl)cc3)CC2=O)CC1] |
| 43 | 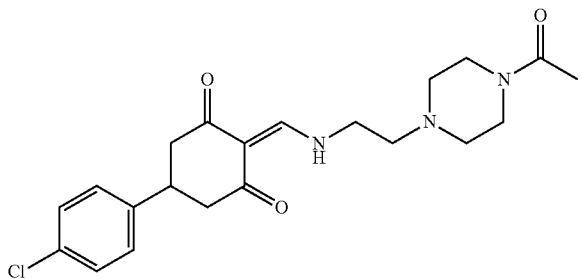 [SMILES: CC(=O)N1CCN(CCNC=C2C(=O)CC(c3ccc(Cl)cc3)CC2=O)CC1] |

| Compound | Structure |
|---|---|
| 44 | 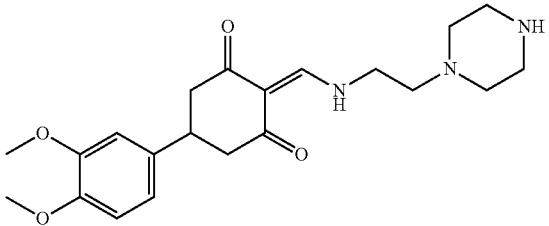 [SMILES: COc1ccc(C2CC(=O)C(=CNCCN3CCNCC3)C(=O)C2)cc1OC] |
| 45 | 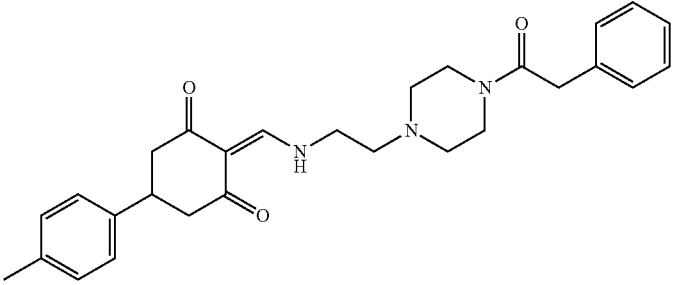 [SMILES: Cc1ccc(C2CC(=O)C(=CNCCN3CCN(C(=O)Cc4ccccc4)CC3)C(=O)C2)cc1] |
| 46 | 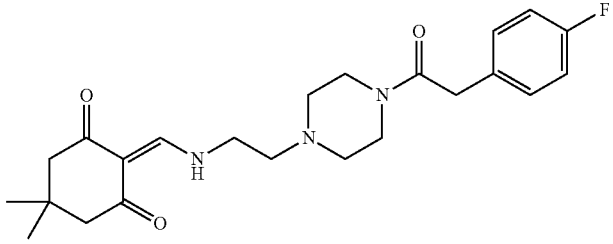 [SMILES: CC1(C)CC(=O)C(=CNCCN2CCN(C(=O)Cc3ccc(F)cc3)CC2)C(=O)C1] |
| 47 | 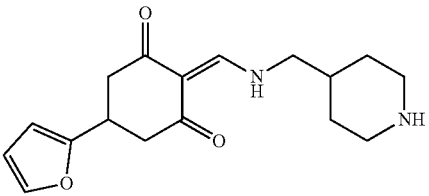 [SMILES: O=C1CC(c2ccco2)CC(=O)C1=CNCC1CCNCC1] |
| 48 | 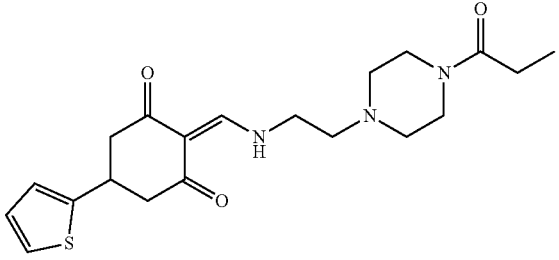 [SMILES: CCC(=O)N1CCN(CCNC=C2C(=O)CC(c3cccs3)CC2=O)CC1] |
| 49 | 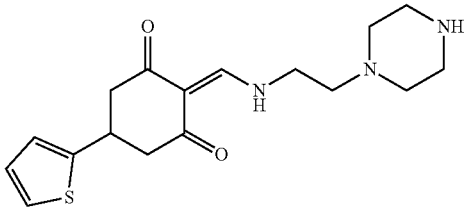 |

-continued

| Compound | Structure |
|---|---|
| 50 | 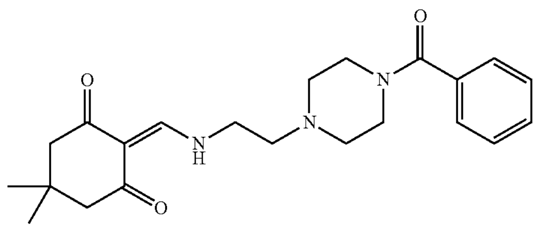 [SMILES: CC1(C)CC(=O)C(=CNCCN2CCN(C(=O)c3ccccc3)CC2)C(=O)C1] |
| 51 | 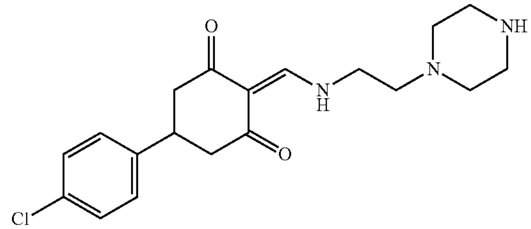 [SMILES: O=C1CC(c2ccc(Cl)cc2)CC(=O)C1=CNCCN1CCNCC1] |
| 52 | 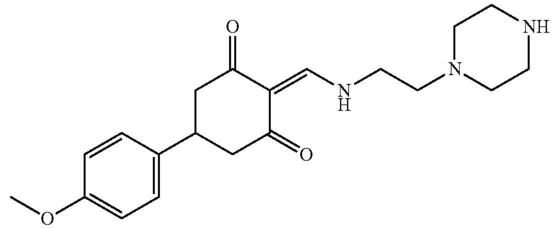 [SMILES: COc1ccc(C2CC(=O)C(=CNCCN3CCNCC3)C(=O)C2)cc1] |
| 53 | 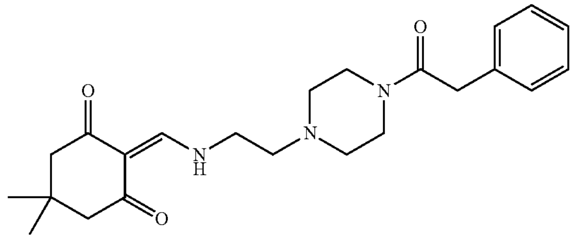 [SMILES: CC1(C)CC(=O)C(=CNCCN2CCN(C(=O)Cc3ccccc3)CC2)C(=O)C1] |
| 54 | 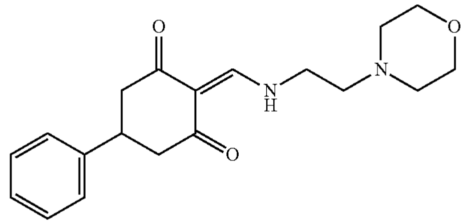 [SMILES: O=C1CC(c2ccccc2)CC(=O)C1=CNCCN1CCOCC1] |
| 55 | 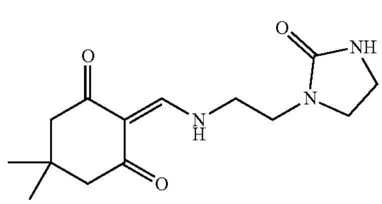 [SMILES: CC1(C)CC(=O)C(=CNCCN2CCNC2=O)C(=O)C1] |

-continued
| Compound | Structure |
|---|---|
| 56 | 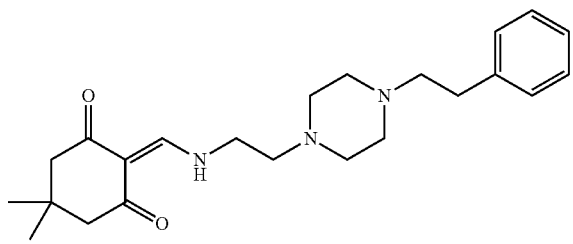 [SMILES: CC1(C)CC(=O)C(=CNCCN2CCN(CCc3ccccc3)CC2)C(=O)C1] |
| 57 | 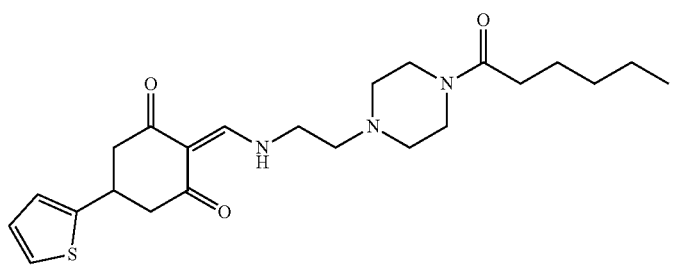 |
| 58 | 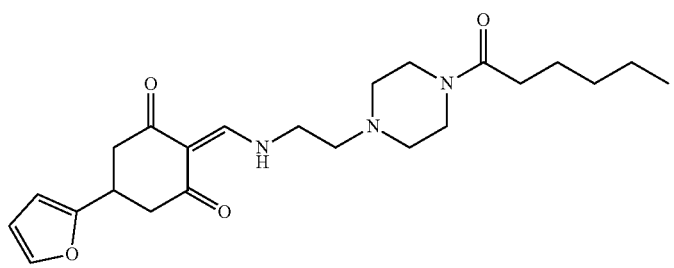 [SMILES: CCCCCC(=O)N1CCN(CCNC=C2C(=O)CC(c3ccco3)CC2=O)CC1] |
| 59 | 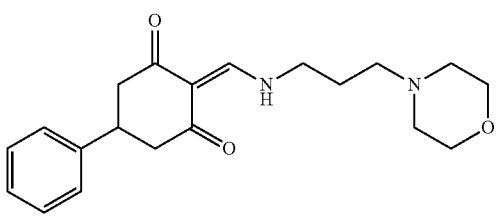 [SMILES: O=C1CC(c2ccccc2)CC(=O)C1=CNCCCN1CCOCC1] |
| 60 | 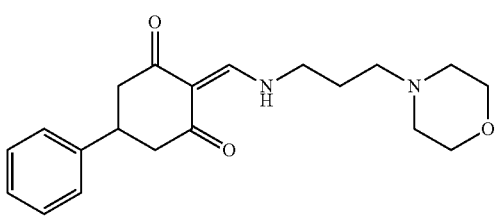 [SMILES: O=C1CC(c2ccccc2)CC(=O)C1=CNCCCN1CCOCC1] |
| 61 | 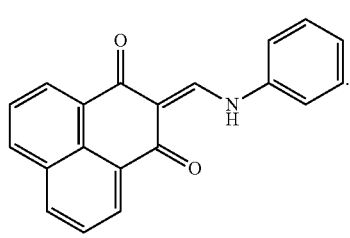 [SMILES: O=c1c(=CNc2ccccc2)c(=O)c2cccc3cccc1c32] |

In a specific embodiment, the drug for modulating autophagy is a modulator of a mammalian ATG8 homologous protein (especially LC3B).

In a specific embodiment, the drug for modulating autophagy is a drug for treating a disease associated with autophagy, particularly a mammalian ATG8 homologous protein (especially LC3B).

In a second aspect, the present invention provides a method for modulating the activity of a mammalian ATG8 homologous protein (especially LC3B), where the compound or a salt thereof is used alone or in combination with other drugs to modulate the interaction of LC3B and mammalian ATG8 homologous proteins with other proteins in the body. The method may be carried out in vivo or in vitro.

In a third aspect, the present invention provides a method for modulating autophagy, which comprises the step of administering the above-mentioned compound or a salt thereof alone or in combination with other drugs.

In a fourth aspect, the present invention provides a method for treating a disease associated with autophagy, particularly a mammalian ATG8 homologous protein (particularly LC3B), which comprises the step of administering the above-mentioned compound or a salt thereof alone or in combination with other drugs to a patient in need thereof.

The mammalian ATG8 homologous protein includes proteins of LC3, GABARAP and GATE-16 subfamilies. In human body, the LC3 family includes LC3A, LC3B and LC3C, the GABARAP family includes GABARAPL and GABARAPL1, and the GATE-16 family includes GABARAPL2.

Preferably, the disease associated with autophagy includes: tumors, such as liver cancer, lung cancer, pancreatic cancer, breast cancer, cervical cancer, endometrial cancer, colorectal cancer, gastric cancer, lung cancer, nasopharyngeal carcinoma, ovarian cancer, prostate cancer, leukemia, lymphoma, myeloma, and others; cardiovascular disease; autoimmune disease; neurodegenerative disease; hypertension; bone tissue cell and bone diseases; Crohn's disease; acute kidney injury; cerebral ischemia; retinal disease; bronchial asthma; Vici syndrome; and infectious diseases, such as AIDS.

The other drugs are commercially available, including, but not limited to, ibrutinib, imatinib, gemcitabine, erlotinib, pemetrexed disodium, AZD3759 and lenalidomide.

DETAILED DESCRIPTION OF THE PREFERRED EMBODIMENTS

Figure 1:
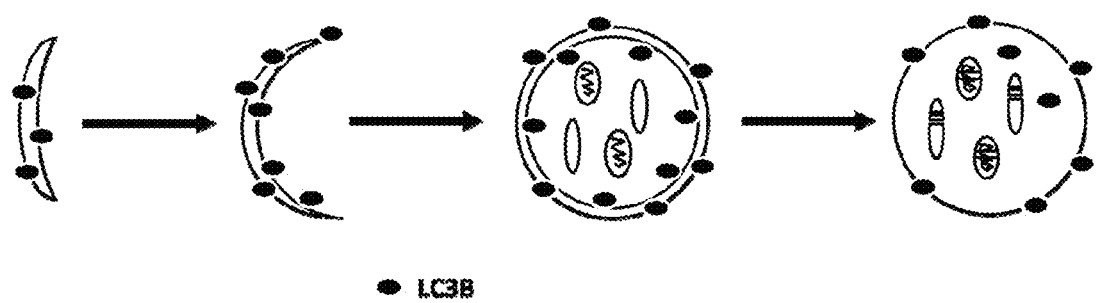
FIG. 1 shows the role of LC3B in autophagy.

In the present invention, by designing a FITC-labeled peptide and a GST fusion protein expressing LC3B, a high-throughput screening platform based on fluorescence polarization is established, and a high-throughput screening of a compound library therewith revealed that an aminomethylenecyclohexane-1,3-dione compound or a salt thereof is useful as a modulator targeting a mammalian ATG8 homologous protein (especially LC3B). In addition, by the immunoblotting of LC3-I/LC3-II protein, immunofluorescence staining and fluorescence microscopy, the above-mentioned compound or a salt thereof is confirmed to have the ability to modulate autophagy, and thus can be used for modulating autophagy and treating relevant diseases. Hereinafter, the present invention is described in detail by way of examples.

The terms used in the present invention have their general meaning in the art, and in the case of conflict, the definitions in this application apply. The chemical names, generic names and chemical structures are used interchangeably to describe the same structure. These definitions apply regardless of whether they are used alone or in combination with other terms. Thus, the definition of "$C_{1-6}$ alkyl" applies to the "$C_{1-6}$ alkyl" and the "$C_{1-6}$ alkyl" moiety of "$C_{1-6}$ hydroxyalkyl", "$C_{1-6}$ haloalkyl", "$C_{1-6}$ alkoxy" and the like.

In the present invention, the drug for modulating autophagy and treating diseases associated with autophagy may be a pharmaceutical composition. "Pharmaceutical composition" means a composition suitable for administration to a patient. The composition may comprise a single compound of the present invention, or a mixture of the compounds of the present invention, or a salt, a solvate, a prodrug, an isomer or a tautomer of the compound of the present invention, or the compound of the present invention in combination with one or more pharmaceutically acceptable carriers or excipients. The "patients" include humans and non-human animals. The pharmaceutical composition may be in various forms such as tablets, capsules, powders, syrups, solutions, suspensions, aerosols, and the like, and may be present in a suitable solid or liquid carrier or diluent and in a sterilized container suitable for injection or infusion.

Various dosage forms of the pharmaceutical composition of the present invention can be prepared according to conventional preparation methods in the pharmaceutical field. The formulation of the preparation comprises, in a unit dosage, 0.05-200 mg of the compound of General Formula (I), and preferably 0.1-100 mg of the compound of General Formula (I).

The compound and pharmaceutical composition of the present invention can be used clinically in mammals, including humans and animals, and can be given through the routes of administration including oral, intranasal, transdermal, transpulmonary, or gastrointestinal tract administration, and most preferably oral administration. The most preferred daily dose is 0.01-200 mg/kg body weight in a single dose, or 0.01-100 mg/kg body weight in divided doses. Regardless of the route of administration, the optimal dosage for an individual depends on the particular treatment. Generally, the most suitable dose is found by starting with a small dose, and then gradually increasing the dose.

"Halo" refers to fluoro, chloro, bromo, or iodo.

"$C_{1-6}$ alkyl" refers to a linear or branched alkyl group having 1 to 6 carbon atoms, and preferably a linear or branched alkyl group having 1 to 4 carbon atoms. "Branched" means that an alkyl group of one or more carbon atoms, such as methyl, ethyl or propyl, is attached to a linear alkyl group. Preferably $C_{1-6}$ alkyl groups include, but are not limited to, methyl, ethyl, n-propyl, isopropyl, n-butyl, isobutyl and t-butyl groups.

"$C_{1-6}$ haloalkyl" refers to a C1-6 alkyl group as defined above, which comprises one or more halogen substituents. Preferably $C_{1-6}$ haloalkyl groups include, but are not limited to, trifluoromethyl.

"$C_{1-6}$ hydroxyalkyl" refers to a C1-6 alkyl group as defined above, which comprises one or more hydroxyl groups. Preferably C1-6 hydroxyalkyl groups include, but are not limited to, hydroxymethyl and 2-hydroxyethyl.

"$C_{1-6}$ alkoxy" refers to a $C_{1-6}$ alkyl-O— group, which is attached to a parent moiety via the oxygen atom, in which the $C_{1-6}$ alkyl group is as defined above. Preferably $C_{1-6}$ alkoxy groups include, but are not limited to, methoxy, ethoxy, n-propoxy, isopropoxy and n-butoxy.

"$C_{6-10}$ aryl" refers to an aromatic monocyclic or polycyclic ring system having 6 to 10 carbon atoms. Preferably C6-10 aryl groups include, but are not limited to, phenyl and naphthyl.

"$C_{3-7}$ cycloalkyl" refers to a non-aromatic saturated monocyclic or polycyclic group having 3 to 7 carbon atoms and preferably 3 to 6 carbon atoms in the ring. Preferably monocyclic C3-7 cycloalkyl groups include, but are not limited to, cyclopropyl, cyclopentyl, cyclohexyl, cycloheptyl, and the like.

"5-10 membered heteroaryl" refers to an aromatic monocyclic or polycyclic group having 5 to 10 ring atoms, and the 5-10 membered heteroaryl group comprises 1 to 4 heteroatoms selected from N, O and S. Preferably a 5-10 membered heteroaryl group comprises 5 to 6 ring atoms. The nitrogen atom in the 5-10 membered heteroaryl groups can be optionally oxidized into a corresponding N-oxide. Preferably C5-10 heteroaryl groups include, but are not limited to, pyridyl, pyrazinyl, furyl, thienyl, pyrimidinyl, pyridone, oxazolyl, isothiazolyl, oxazolyl, oxadiazolyl, thiazolyl, thiadiazolyl, pyrazolyl, furazanyl, pyrrolyl, triazolyl, 1,2,4-thiadiazolyl, pyridazinyl, quinoxalinyl, phthalazinyl, hydroxyindolyl, imidazo[1,2-a]pyridyl, imidazo[2,1-b]thiazolyl, benzofurazanyl, indolyl, azaindolyl, benzimidazolyl, benzothienyl, quinolyl, imidazolyl, thienopyridyl, quinazolinyl, thienopyrimidinyl, pyrrolopyridyl, imidazopyridine, isoquinolinyl, benzoazinyl, 1,2,4-triazinyl, benzothiazolyl, and oxides thereof. The term "5-10 membered heteroaryl" also refers to partially saturated 5-10 membered heteroaryl, such as, tetrahydroisoquinolyl, tetrahydroquinolyl.

"3-7 membered heterocyclyl" refers to a non-aromatic monocyclic or polycyclic group having 3 to 7 ring atoms, preferably 3 to 6 ring atoms, and more preferably 5 to 6 ring atoms, where the 3-10 membered heterocyclyl group comprises 1 to 4 heteroatoms selected from N, O and S. The nitrogen or sulfur atom in the 3-10 membered heterocyclyl groups can be optionally oxidized into a corresponding N-oxide, S-oxide or S-dioxide. Therefore, the term "oxide" in the present invention refers to the corresponding N-oxide, S-oxide or S-dioxide. The "3-7 membered heterocyclyl" also includes a group in which two available hydrogen atoms on the same carbon atom of the ring are replaced by a single group =O (i.e. forming a carbonyl group), which may be referred to as "oxo" in the present invention. Preferably monocyclic 3-7 membered heterocycloalkyl groups include, but are not limited to, piperidinyl, oxetanyl, pyrrolyl, piperazinyl, morpholinyl, thiomorpholinyl, thiazolidinyl, 1,4-dioxanyl, tetrahydrofuryl, tetrahydrothiophenyl, a lactam group (such as pyrrolidinonyl), a lactone group having 3 to 7 ring atoms, and oxides thereof.

"Ester group" means a group formed by removing a hydrogen atom from an ester formed by esterification of an aliphatic or aromatic carboxylic acid having 1 to 20 carbon atoms with a primary, secondary, or tertiary alcohol having 1 to 20 carbon atoms. Preferably ester groups include, but are not limited to, a methyl ester group, an ethyl ester group, an isopropyl ester group, a tert-butyl ester group, and a phenyl ester group.

"Amido" refers to a group formed by removing a hydrogen atom from an amide obtained by amidation of an aliphatic or aromatic carboxylic acid having 1 to 20 carbon atoms with a primary or secondary amine having 1 to 20 carbon atoms.

The term "unsubstituted or substituted" means that a particular group is unsubstituted or substituted with one or more substituents. The substituents include, but are not limited to, hydrogen, hydroxyl, amino, cyano, nitro, carboxyl, halo, C1-6 alkyl, C1-6 haloalkyl or C1-6 hydroxyalkyl. Two adjacent substituents can be attached to form C6-10 aryl, 5-10 membered heteroaryl, C3-10 cycloalkyl or 3-10 membered heterocycloalkyl substitutions on groups such as C6-10 aryl, 5-10 membered heteroaryl, C3-10 cycloalkyl, 3-10 membered heterocycloalkyl, and 3-7 membered heterocycloalkenyl include substitutions on any of the ring moieties.

For convenience, only one isomer of each compound is exemplified in the present invention. It should be noted that the compound of the present invention includes all stereoisomers.

The compound of the present invention can form a metal chelate with one or more metal ions, including, but not limited to, copper, iron, magnesium, calcium, zinc, nickel, and platinum. It is to be noted that the compound of the present invention includes all metal chelates.

The term "pharmaceutically acceptable salt" refers to a substance that is suitable for use in humans and/or animals without undue adverse side effects (e.g., toxicity, irritation, and allergies), i.e., having a reasonable benefit/risk ratio. Pharmaceutically acceptable salts include inorganic and organic salts that can be obtained during the final separation and purification of the compound of the present invention, or by reaction of the free acid or base functional group with a suitable base or acid. Acids suitable for salt formation include, but are not limited to, inorganic acids such as hydrochloric acid, phosphoric acid or sulfuric acid, or organic acids such as citric acid, ascorbic acid, tartaric acid, lactic acid, maleic acid, malonic acid, fumaric acid, glycolic acid, succinic acid, propionic acid, acetic acid or methanesulfonic acid. Bases suitable for salt formation include, but are not limited to, inorganic bases such as sodium carbonate, sodium hydroxide, potassium carbonate, potassium hydroxide, lithium hydroxide, calcium acetate, calcium chloride or magnesium chloride, and organic bases such as aminoethanol.

The term "effective amount" means that the amount of the compound of present invention contained in the administered composition is sufficient to modulate (e.g., inhibit or activate) a mammalian ATG8 homolog.

The compound of the present invention can be prepared by various similar known methods in the art, and exemplary schemes for preparing the compound of the present invention are shown in examples below.

EXAMPLES

The present invention is further elaborated below in conjunction with specific examples. It should be understood that these examples are only used to illustrate the present invention and are not intended to limit the scope of the present invention, and the present invention is not limited thereto. Those skilled in the art will readily appreciate that these compounds can be prepared using known variations of the conditions and procedures in the following preparative methods. The starting reactants used in the present invention are commercially available unless otherwise stated.

General Synthesis Method:

Unless otherwise stated, all reactions are carried out under an inert gas atmosphere (such as argon or nitrogen), and the commercially available reagents and anhydrous solvents are used without further treatment.

The mass spectrum is recorded on liquid chromatograph-mass spectrometer (LC-MS, Agilent 6120B single quadrupole liquid chromatograph-mass spectrometer). The $^1$H NMR spectrum is recorded on Bruker AMX-400 NMR Spectrometer, in deuterated dimethyl sulfoxide (DMSO-d6) with the deuterated solvent peaks as a reference. The chemical shift δ is in ppm, the coupling constant (J or J) is in Hertz (Hz), and the coupling and split peaks in the NMR spectrum are expressed as: broad singlet (brs), singlet (s), doublet (d), doublet of doublets (dd), triplet (t), quartet (q) and multiplet (m).

Example 1: Synthesis of Compound 2-((Dimethyl-amino)Methylene)-5-Phenyl-Cyclohexane-1,3-Dione (Compound 1)

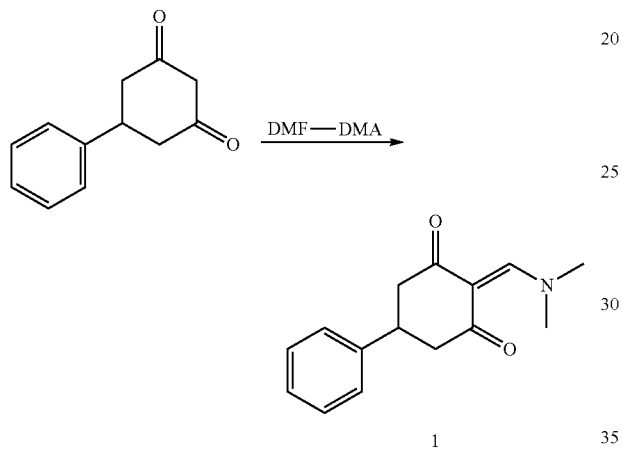

The compound 5-phenylcyclohexane-1,3-dione (5.0 g, 26.6 mmol) was dissolved in chloroform (25 mL), and then N,N-dimethylformamide dimethylacetal (DMF-DMA) (5 mL) was added and reacted for 1 hr at room temperature. After reaction, the reaction solution was concentrated, and the concentrate was homogenized in 10% ethyl acetate (EA)/petroleum ether (PE) to produce a precipitate. The precipitate was filtered, and dried to obtain the target compound (4.81 g, yield 74%). Compound 1: $^1$H NMR (400 MHz, DMSO-d6) δ 8.04 (s, 1H), 7.32 (d, J=4.3 Hz, 4H), 7.25-7.17 (m, 1H), 3.43 (s, 3H), 3.32-3.24 (m, 1H), 3.09 (s, 3H), 2.70-2.61 (m, 2H), 2.53-2.51 (m, 1H), 2.49-2.46 (m, 1H); MS: 244.2 [M+1].

Example 2: Synthesis of Compound 5-Phenyl-2-((Phenylamino)Methylene)-Cyclohexane-1,3-Dione (Compound 11)

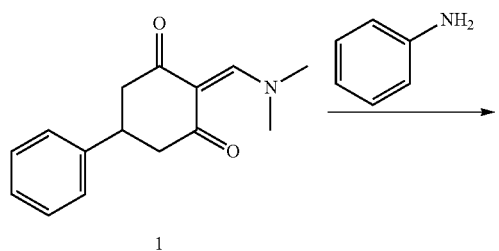

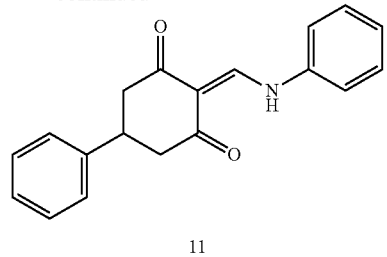

The compound 2-(dimethylamino)methylene)-5-phenyl-cyclohexane-1,3-dione (200 mg, 0.82 mmol)(compound 1), aniline (60 mg, 0.65 mmol), and acetic acid (0.5 mL) were dissolved in ethanol (10 mL), and reacted for 1 hr under reflux. After cooling to room temperature, the reaction solution was concentrated to give a crude product, which was separated by column chromatography to obtain the target compound (150 mg, yield 79%). Compound 11: $^1$H NMR (400 MHz, DMSO-d6) δ 8.72 (s, 1H), 7.49-7.41 (m, 4H), 7.35-7.28 (m, 5H), 7.25-7.22 (m, 1H), 3.46-3.40 (m, 1H), 2.95-2.70 (m, 4H); MS: 292.1 [M+1].

Example 3

The compounds 2-10 and 12-61 can be prepared by the above synthesis methods using the corresponding substituted 1,3-cyclohexandione and corresponding amino compounds.

Example 4: Molecular Level Experiments of Targeting LC3B of Compounds or Salts Thereof By constructing a prokaryotic expression system, the LC3B protein was expressed and purified, and a preliminary screening and verification platform was established using fluorescence polarization experiments to determine the activity of synthesized small compound libraries.

The recombinant protein GST-LC3B (final concentration 180 nM, SEQ ID NO: 1) and N-terminal FITC-labeled peptide (SEQ ID NO: 2, final concentration 18 nM) were placed in the FP buffer (50 mM HEPES pH 7.5, 0.1 mg/mL BSA and 1 mM DTT), to which a compound serially diluted with the FP buffer was added. Then the resulting mixture was incubated at 25° C. in the dark. The fluorescence polarization value (PerkinElmer Envision, emission wavelength 480 nm; absorption wavelength 535 nm) was monitored, and the IC$_{50}$ value was calculated using the GraphPad Prism 6.0 program.

The test results are shown in Table 1. The IC$_{50}$ values of the compounds are interpreted as follows. Where 100 μM<IC$_{50}$≤1 mM, the compound is considered to be less active for LC3B (+); where 15 μM<IC$_{50}$≤100 μM, the compound is considered to be moderately active for LC3B (++); where 3 μM<IC$_{50}$≤15 μM, the compound is considered to be highly active for LC3B (+++); and where IC$_{50}$≤3 μM, the compound is considered to be more highly active for LC3B (++++).

TABLE 1

Activity data of the compounds in modulation of LC3B

| Compound | IC$_{50}$ | Compound | IC$_{50}$ | Compound | IC$_{50}$ | Compound | IC$_{50}$ | Compound | IC$_{50}$ |
|---|---|---|---|---|---|---|---|---|---|
| 1  | +++ | 2  | ++  | 3  | +++ | 4  | +++ | 5  | +++ |
| 6  | +++ | 7  | +++ | 8  | +   | 9  | +++ | 10 | +++ |
| 11 | ++  | 12 | ++  | 13 | +++ | 14 | +++ | 15 | ++  |
| 16 | ++  | 17 | +   | 18 | +   | 19 | +   | 20 | +   |
| 21 | +   | 22 | +   | 23 | +   | 24 | +   | 25 | +   |
| 26 | +   | 27 | +   | 28 | +   | 29 | +   | 30 | +   |
| 31 | +++ | 32 | +++ | 33 | +++ | 34 | +   | 35 | +++ |
| 36 | +   | 37 | +++ | 38 | +++ | 39 | +++ | 40 | +++ |
| 41 | +   | 42 | +++ | 43 | +++ | 44 | +++ | 45 | +++ |
| 46 | +   | 47 | +++ | 48 | +++ | 49 | +++ | 50 | +   |
| 51 | +++ | 52 | +++ | 53 | +   | 54 | +++ | 55 | +   |
| 56 | +   | 57 | +++ | 58 | +++ | 59 | +++ | 60 | +++ |
| 61 | ++  |    |     |    |     |    |     |    |     |

Example 5: Modulation of Autophagy by Compounds or Salts Thereof

Immunoblotting of LC3-I/LC3-II Protein

Hela cells were inoculated into a 6-well plate, cultured overnight, and treated for 12 hrs. by adding a certain concentration of a compound. Then, the medium was replaced by a serum-free medium, and the cells were starved for 24 hrs. The medium was aspirated off, and the cells were washed once with PBS. SDS-PAGE was added, and the cells were lysed by 2× sample buffer. The sample was boiled at 99° C. for 10 min, separated by SDS-PAGE, and detected for LC3-I/LC3-II using the LC3B antibody (Novus). The results are shown in FIG. 2A.

Figure 2:
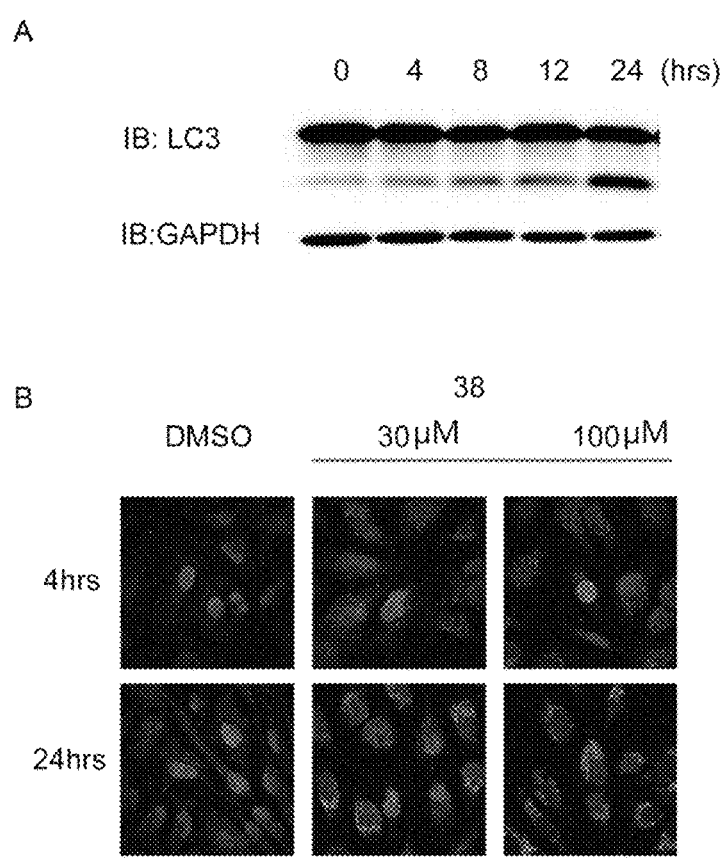
FIG. 2 shows the effect of the compound 38 on autophagy.

As can be seen from FIG. 2A, LC3-II accumulates with the elapse of time of treatment with the compound.

Immunofluorescence Staining and Fluorescence Microscopy

The Hela cells were inoculated onto a glass cover in a 6-well plate, cultured until the cells were in good condition and treated for 12 hrs. by adding a certain concentration of a compound. Then, the medium was replaced by a serum-free medium, and the cells were starved for 24 hrs. The cells were previously cooled for 10 min, perforated with 0.2% Triton X-100, and stood for 10 min at room temperature. The cells were blocked with 2.5% BSA in PBS, and incubated overnight with a 4-titer primary anti-LC3B antibody. Then the primary antibody was identified with a fluorescent secondary antibody, and the nucleus was stained with DAPI. The cells were photographed under a microscope. The test results are shown in FIG. 2B.

As can be seen from FIG. 2B, compared with the control group, the autophagosome accumulates after treatment with the compound 38, and the higher the concentration is, the larger the accumulation will be.

Example 6: Inhibition of Compounds or Salts Thereof Used in Combination with Some Commercially Available Drugs on Proliferation of Various Tumor Cells Tumor cell lines: Large B lymphoma cell lines (DB, Toledo, Pfeiffer, SU-DHL6, WSU-DLCL2, OCI-Lyl9, SU-DHL2, and SU-DHL8), Mantle cell lymphoma cell lines (REC-1, Z-138, Jeko-1, and Maver-1), Pancreatic cancer cell lines (AsPC-1, BxPC-3, MIAPaCa-2, Panc-3.014, CaPan-1, and Panc-1), Colon cancer cell line HCT116, Non-small cell lung cancer cell lines (PC9, HCC827, and NCI-H1975) and Multiple myeloma cell lines (H929, KMS26, and RPMI-8226).

The commercially available drugs used in combination: Ibrutinib, Imatinib, Gemcitabine, Erlotinib, Pemetrexed disodium, AZD3759, and Lenalidomide.

Figure 3:
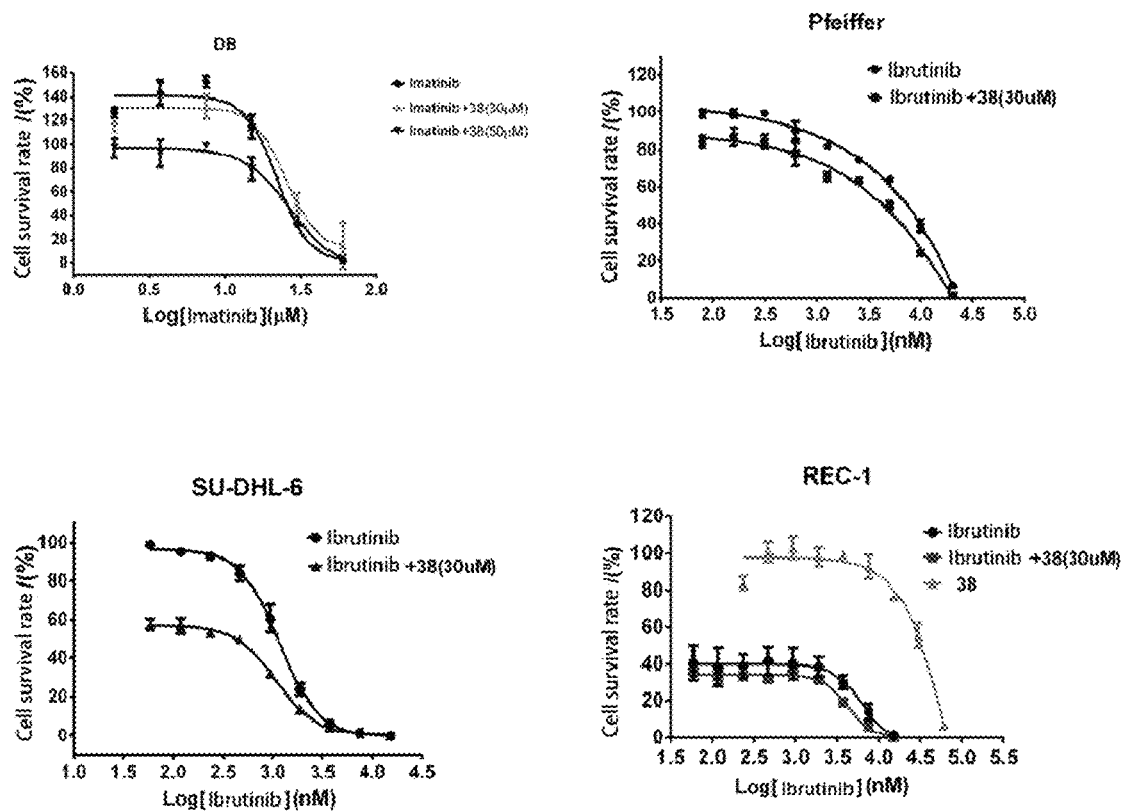
FIG. 3 shows the effect of the compound 38 combined with some of the commercially available drugs on the proliferation of some tumor cells.

Experimental method: A complete medium containing 10% FBS was used. The cells were counted, inoculated into a 96-well plate at about 10000 cells/100 μl per well, and treated with a commercially available drug and the compound 38, where the drug was 1:3 serially diluted, and the concentration of the compound 38 was set to 100 μM, 50 μM, and 30 μM. The change in cell proliferation was measured by Cell Titer-Glo method after 72 hrs. of administration. The cell survival rate as a longitudinal coordinate was plotted against the drug concentration as horizontal coordinate. The results are shown in FIG. 3.

The cell survival rate is calculated by a formula: Survival rate (%)=(OD of treatment well−OD of blank well)/(OD of control well−OD of blank well)×100.

The detection results are shown in Table 2, in which: "++++" indicates that the combined effect is very obvious at 30 μM; "+++" indicates that the combined effect is obvious at 50 μM; "++" indicates that the combined effect is obvious at 100 μM; and "+" indicates that the combined effect is not obvious at 100 μM.

TABLE 2

Effect of compound 38 combined with commercially available drugs on proliferation of various tumor cells

| Tumor | Cell line | Drug used in combination | Combined effect |
|---|---|---|---|
| Large B lymphoma | DB | Ibrutinib | +++ |
|  |  | Imatinib | +++ |
|  | Toledo | Ibrutinib | ++++ |
|  |  | Imatinib | +++ |
|  | Pfeiffer | Ibrutinib | ++++ |
|  | SU-DHL6 | Ibrutinib | ++++ |
|  | WSU-DLCL2 | Ibrutinib | +++ |
|  | OCI-Ly19 | Ibrutinib | ++ |
|  | SU-DHL2 | Ibrutinib | ++++ |
|  | SU-DHL8 | Imatinib | +++ |
| Mantle cell lymphoma | REC-1 | Ibrutinib | ++++ |
|  | Z-138 | Ibrutinib | + |
|  | Jeko-1 | Ibrutinib | + |
|  | Maver-1 | Ibrutinib | ++ |
| Pancreatic cancer | AsPC-1 | Gemcitabine | ++ |
|  |  | Imatinib | ++ |
|  |  | Erlotinib | +++ |
|  | BxPC-3 | Gemcitabine | ++ |
|  |  | Imatinib | ++ |
|  |  | Erlotinib | ++ |

TABLE 2-continued

Effect of compound 38 combined with commercially available drugs on proliferation of various tumor cells

| Tumor | Cell line | Drug used in combination | Combined effect |
|---|---|---|---|
| | MIAPaCa-2 | Gemcitabine | + |
| | | Imatinib | ++ |
| | | Erlotinib | +++ |
| | Panc-3.014 | Gemcitabine | + |
| | | Imatinib | ++ |
| | | Erlotinib | ++ |
| | CaPan-1 | Gemcitabine | + |
| | | Imatinib | ++ |
| | | Erlotinib | +++ |
| | Panc-1 | Gemcitabine | ++ |
| | | Imatinib | ++ |
| | | Erlotinib | ++ |
| Colon cancer | HCT116 | Gemcitabine | ++ |
| | | Imatinib | +++ |
| Non-small cell lung cancer | PC9 | Erlotinib | +++ |
| | | Pemetrexed disodium | + |
| | | AZD3759 | + |
| | HCC827 | Erlotinib | + |
| | | Pemetrexed disodium | + |
| | | AZD3759 | ++ |
| | NCI-H1975 | Erlotinib | + |
| | | Pemetrexed disodium | + |
| | | AZD3759 | + |
| Multiple myeloma | H929 | Lenalidomide | ++++ |
| | KMS26 | Lenalidomide | + |
| | RPMI-8226 | Lenalidomide | ++ |

What is claimed is:

1. A method for inhibiting LC3 proteins in a human body comprising:

treating the human body with a compound or a pharmaceutically acceptable salt thereof, alone or in combination with other drugs, to inhibit the LC3 proteins, wherein the LC3 proteins are selected from the group consisting of LC3A, LC3B and LC3C proteins, and wherein the compound is selected from the group consisting of the following compounds:

| Compound | Structure |
|---|---|
| 1 | 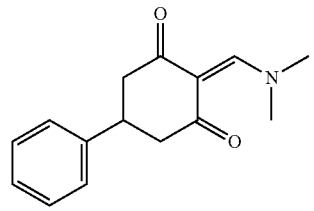 [SMILES: CN(C)C=C1C(=O)CC(c2ccccc2)CC1=O] |
| 2 | 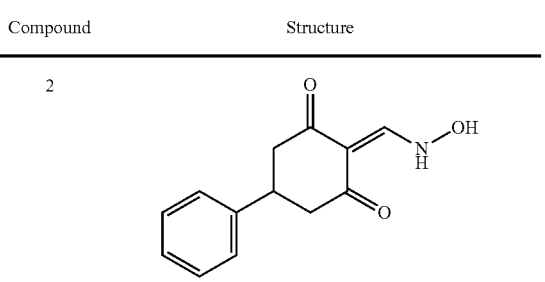 |
| 3 | 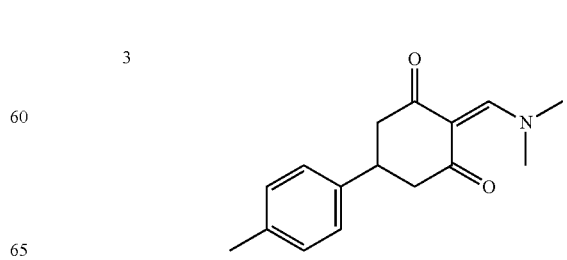 |

| Compound | Structure |
|---|---|
| 4 | 4-F-phenyl substituted 2-((dimethylamino)methylene)cyclohexane-1,3-dione |
| 5 | 4-Cl-phenyl substituted 2-((dimethylamino)methylene)cyclohexane-1,3-dione |
| 6 | 2-methoxyphenyl substituted 2-((dimethylamino)methylene)cyclohexane-1,3-dione |
| 7 | 2-bromophenyl substituted 2-((dimethylamino)methylene)cyclohexane-1,3-dione |

2. The method as claimed in claim 1, wherein the other drugs are selected from the group consisting of ibrutinib, imatinib, gemcitabine, erlotinib, pemetrexed disodium, AZD3759 and lenalidomide.

* * * * *